United States Patent [19]

Heckel et al.

[11] Patent Number: 5,391,556

[45] Date of Patent: Feb. 21, 1995

[54] BENZIMIDAZOLYL DERIVATIVES, PHARMACEUTICAL COMPOSITIONS CONTAINING THESE COMPOUNDS AND PROCESSES FOR PREPARING THEM

[75] Inventors: Armin Heckel, Biberach; Robert Sauter, Laupheim; Manfred Psiorz, Ingelheim am Rhein; Klaus Binder, Warthausen; Thomas Mueller, Biberach; Rainer Zimmermann, Mittelbiberach, all of Germany

[73] Assignee: Karl Thomae GmbH, Biberach an der Riss, Germany

[21] Appl. No.: 14,598

[22] Filed: Feb. 8, 1993

[30] Foreign Application Priority Data

Feb. 13, 1992 [DE] Germany .......................... 4204270

[51] Int. Cl.$^6$ .................. C07D 401/12; C07D 401/06; A61K 31/445; A61K 31/44
[52] U.S. Cl. ................... 514/322; 514/338; 546/199; 546/271
[58] Field of Search ................ 546/199, 271; 514/322, 514/338

[56] References Cited

FOREIGN PATENT DOCUMENTS

| 0097630 | 1/1984 | European Pat. Off. ............ 544/160 |
| WO9208709 | 5/1992 | European Pat. Off. ............ 544/386 |
| 2007663 | 5/1979 | United Kingdom ................ 544/370 |

OTHER PUBLICATIONS

Chemical Abstracts, vol. 113, 1990, abstract No. 6182j, Okada M. et al. "Preparation of 1,2,3,4-tetrahydroisoquinoline derivatives as antithrombotics", an abstract of JP-A-2 009 863, published on 12 Jan. 1990.

Wagner, G. et al, in Pharmazie, vol. 36, No. 9, 597–603 (Sep., 1981).

Wagner, G. et al, in Pharmazie, vol. 36, No. 9, 639–641 (Sep., 1981).

*Primary Examiner*—Alan L. Rotman
*Attorney, Agent, or Firm*—Robert P. Raymond; Alan R. Stempel; Mary-Ellen M. Timbers

[57] ABSTRACT

The invention relates to benzimidazolyl derivatives of general formula

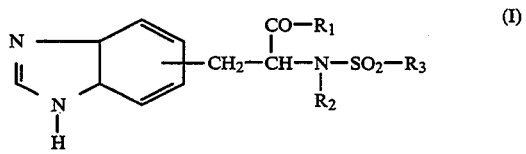

(I)

wherein $R_1$ to $R_3$ are defined as in claim 1, the mixtures of position isomers thereof and the salts thereof, which have valuable pharmacological properties, particularly the effect of extending the thrombin time, a thrombin inhibiting effect and an inhibiting effect on related serine proteases such as trypsin, pharmaceutical compositions containing this compound and processes for the preparation thereof.

7 Claims, No Drawings

BENZIMIDAZOLYL DERIVATIVES, PHARMACEUTICAL COMPOSITIONS CONTAINING THESE COMPOUNDS AND PROCESSES FOR PREPARING THEM

The present invention relates to benzimidazolyl derivatives of the general formula

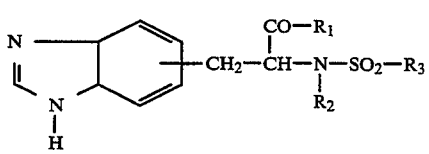

the mixtures of position isomers thereof and the salts thereof, more particularly the physiologically acceptable salts thereof with inorganic or organic acids or bases, which have valuable pharmacological properties, particularly the effect of extending the thrombin time, a thrombin-inhibiting effect and an inhibitory effect on related serine proteases such as trypsin, as well as pharmaceutical compositions containing these compounds and processes for preparing them.

In general formula I above $R_1$ denotes an amino group disubstituted by alkyl groups in which an alkyl group may be substituted by a phenyl group, a pyrrolidino, piperidino or hexamethyleneimino group optionally substituted by a phenyl, hydroxy, carboxy, alkylcarbonyl, aminocarbonyl, cyano or N-alkanoylalkylamino group, wherein the hydroxy group may not be in the α-position to the ring nitrogen atom, one of the above-mentioned piperidino groups may additionally be substituted by an alkyl group and, in addition, the methylene group in the 4-position of the piperidino group may be replaced by an oxygen atom or by a carbonyl, sulphinyl, imino or N-alkyl-imino group, or an ethylene group in the 3,4-position of the piperidino group or in the 4,5-position of the hexamethyleneimino group may be replaced by an ethenylene, thiophenylene or thiazolylene group, a piperidino group substituted by one, two or three alkyl groups wherein the alkyl substituents may be identical or different, a tetrahydro-4H-thiazolo[4,5-d]azepin-6-yl or tetrahydro-thiazolo[4',5':5,4]thieno[3,2-c]pyridin-7-yl group optionally substituted in the 2-position by an amino group, $R_2$ denotes a hydrogen atom or an alkyl group and $R_3$ denotes a phenyl group optionally substituted by a fluorine, chlorine or bromine atom or by an alkyl, nitro, amino, alkylamino, dialkylamino, phenyl or cyclohexyl group, whilst the phenyl substituent may also be substituted by a fluorine, chlorine or bromine atom or by a nitro or amino group, a phenyl group disubstituted by fluorine, chlorine or bromine atoms or by alkyl or alkoxy groups, whilst one of the substituents may also denote a nitro or amino group, a phenyl group substituted by a hydroxy, amino, alkylamino, dialkylamino or pyrrolyl group, whilst at the same time the phenyl group is substituted by two chlorine or bromine atoms or by two $C_{1-4}$-alkyl groups and the pyrrolyl group may be substituted by one or two alkyl groups, a naphthyl group optionally mono- or disubstituted by hydroxy, alkoxy or dialkylamino groups, an optionally alkyl-substituted indanyl, quinolyl, 1,2,3,4-tetrahydro-quinolyl, isoquinolyl, 1,2,3,4-tetrahydro-isoquinolyl, carbazolyl, 1,2,3,4-tetrahydrocarbazolyl or dibenzofuranyl group, wherein an imino group may additionally be substituted by an alkyl group which may simultaneously be substituted by a carboxy or alkoxycarbonyl group, whilst, unless otherwise specified, the alkyl, alkanoyl and alkoxy moieties mentioned in the definition of groups $R_1$ to $R_3$ may each contain 1 to 3 carbon atoms.

As examples of the definitions of groups $R_1$ to $R_3$ given hereinbefore $R_1$ may denote a dimethylamino, diethylamino, di-n-propylamino, diisopropylamino, N-ethyl-methylamino, N-benzyl-methylamino, N-benzyl-ethylamino, N-benzylisopropylamino, pyrrolidino, 3-methyl-pyrrolidino, 3-ethyl-pyrrolidino, 3-isopropyl-pyrrolidino, piperidino, 4-methyl-piperidino, 4-ethyl-piperidino, 4-n-propylpiperidino, 4,4-dimethyl-piperidino, 4,4-diethyl-piperidino, 2,4,6-trimethyl-piperidino, N-methyl-indan-1-yl-amino, N-ethyl-indan-1-yl-amino, N-isopropyl-indan-1-yl-amino, 5,6,7,8-tetrahydro-thiazolo[4',5':5,4]-thieno[3,2-c]pyridino, 4,5,6,7-tetrahydrothieno[3,2-c]pyridino, 5,6,7,8-tetrahydro-4H-thiazolo[4,5-d]azepino, 5,6,7,8-tetrahydro-4H-thieno[2,3-d]azepino, 5,6,7,8-tetrahydrothiazolo[4',5':5,4]thieno[3,2-c]pyridino, 2-amino-5,6,7,8-tetrahydro-thiazolo[4',5':5,4]thieno[3,2-c]-pyridino, morpholino, 2-methyl-morpholino, 2-ethylmorpholino, 2-phenyl-morpholino, thiomorpholino, 1-oxido-thiomorpholino, 4-(N-acetyl-methylamino)piperidino, 4-(N-acetyl-ethylamino)-piperidino, 4-(N-acetyl-n-propylamino)-piperidino, 4-(N-propionylmethylamino)-piperidino, 4-(N-propionyl-ethylamino)piperidino, 4-(N-propionyl-n-propylamino)-piperidino, 2,3,4,5,6,7-hexahydro-1H-azepino, 1,2,3,6-tetrahydropyridino, 4-methyl-1,2,3,6-tetrahydropyridino, 4-ethyl-1,2,3,6-tetrahydropyridino, 4-isopropyl-1,2,3,6-tetrahydro-pyridino, 4-phenyl-1,2,3,6-tetrahydro-pyridino, 2-carboxy-piperidino, 2-carbmethoxy-piperidino, 2-carbethoxy-piperidino, 2-carbisopropoxy-piperidino, 2-carboxy-4-methylpiperidino, 2-carboxy-4-ethyl-piperidino, 2-carboxy-4-n-propyl-piperdino, 2-carbmethoxy-4-methyl-piperidino, 2-carbmethoxy-4-ethyl-piperidino, 2-carbmethoxy-4-n-propyl-piperidino, 2-carbethoxy-4-methyl-piperidino, 2-carbethoxy-4-ethyl-piperidino, 2-carbisopropoxy-4-n-propyl-piperidino, 2-carbisopropoxy-4-methyl-piperidino, 2-carbisopropoxy-4-ethyl-piperidino, 2-carbisopropoxy-4-n-propyl-piperidino, 4-amino-piperidino, 4-methylaminopiperidino, 4-ethylamino-piperidino, 4-n-propylaminopiperidino, 4-dimethylamino-piperidino, 4-diethylaminopiperidino, 4-cyano-piperidino, 4-hydroxy-piperidino, 4-oxo-piperidino, piperazino, 4-methyl-piperazino, 4-ethyl-piperazino, 4-n-propyl-piperazino or 4-isopropyl-piperazino group, $R_2$ may denote a hydrogen atom, a methyl, ethyl, n-propyl or isopropyl group and $R_3$ may denote a phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-methylphenyl, 3-methylphenyl, 4-methylphenyl, 2-ethylphenyl, 3-ethylphenyl, 4-ethylphenyl, 2-isopropylphenyl, 3-isopropylphenyl, 4-isopropylphenyl, 2-nitrophenyl, 3-nitrophenyl, 4-nitrophenyl, 2-aminophenyl, 3-aminophenyl, 4-aminophenyl, 2-methylaminophenyl, 3-methylaminophenyl, 4-methylaminophenyl, 2-dimethylaminophenyl, 3-dimethylaminophenyl, 4-dimethylaminophenyl, 2-ethylaminophenyl, 3-ethylaminophenyl, 4-ethylaminophenyl, 2-diethylaminophenyl, 3-diethylaminophenyl, 4-diethylaminophenyl, 2-biphenylyl, 3-biphenylyl, 4-biphenylyl, 2-cyclohexylphenyl, 3-cyclohexylphenyl, 4-cyclohexylphenyl, 2'-fluoro-4-biphenylyl, 3'-fluoro-4-biphenylyl, 2'-chloro-4-biphenylyl, 3'-chloro-4-biphenylyl, 2'-bromo-4-biphenylyl, 3'-bromo-4-biphenylyl, 2'-methyl-4-biphenylyl, 3'-methyl-4-biphenylyl, 2'-nitro-4-biphenylyl, 3'-nitro-4-biphenylyl, 2'-amino-4-biphenylyl, 3'-amino-4-biphenylyl, 2'-methylamino-4-biphenylyl, 3'-methylamino-4-biphenylyl, 2'-dimethylamino-4-biphenylyl, 3'-dimethylamino-4-biphenylyl, 3,4-difluorophenyl, 3,4-di-chlorophenyl, 3,4-dibromophenyl, 2,5-dimethylphenyl, 3,4-dimethylphenyl, 3,4-dimethoxyphenyl, 4-chloro-3-nitro-phenyl, 4-bromo-3-nitro-phenyl, 4-hydroxy-3,5-di-tert.butyl-phenyl, 4-amino-3,5-dichlorophenyl, 4-amino-3,5-dibromophenyl, 4-methylamino-3,5-dichlorophenyl, 4-methylamino-3,5-dibromophenyl, 4-ethylamino-3,5-dichlorophenyl, 4-ethylamino-3,5-dibromophenyl, 4-dimethylamino-3,5-dichlorophenyl, 4-dimethylamino-3,5-dibromophenyl, 4-diethylamino-3,5-dichlorophenyl, 4-diethylamino-3,5-dibromophenyl, 3,5-dichloro-4-pyrrolylphenyl, 3,5-dibromo-4-pyrrolyl-phenyl, naphth-1-yl, naphth-2-yl, 1-hydroxy-naphth-1-yl, 1-methoxy-naphth-1-yl, 8-hydroxy-naphth-1-yl, 8-methoxy-naphth-1-yl, 6,7-dimethoxy-naphth-1-yl, 5-amino-naphth-1-yl, 5-methylamino-naphth-1-yl, 5-dimethylamino-naphth-1-yl, dibenzofuryl-(2), dibenzofuryl-(3), carbazol-9-yl, 9-methyl-carbazol-3-yl, 9-ethyl-carbazol-3-yl, 9-hydroxycarbonylmethyl-carbazol-3-yl, 9-methoxycarbonylmethyl-carbazol-3-yl, 9-ethoxycarbonylmethyl-carbazol-3-yl, 9-n-propoxycarbonylmethyl-carbazol-3-yl, 9-methyl-1,2,3,4-tetrahydro-carbazol-6-yl, 1,2,3,4-tetrahydro-quinolin-8-yl, 1,2,3,4-tetrahydro-quinolin-5-yl, 3-methyl-1,2,3,4-tetrahydro-quinolin-8-yl, 3-methyl-1,2,3,4-tetrahydro-quinolin-5-yl, 3-ethyl-1,2,3,4-tetrahydro-quinolin-8-yl, 3-ethyl-1,2,3,4-tetrahydro-quinolin-5-yl, 2-acetyl-1,2,3,4-tetrahydro-quinolin-5-yl, 2-propionyl-1,2,3,4-tetrahydro-quinolin-5-yl, 2-methoxycarbonyl-1,2,3,4-tetrahydro-quinolin-5-yl, 2-ethoxycarbonyl-1,2,3,4-tetrahydro-quinolin-5-yl, 2-isopropoxycarbonyl-1,2,3,4-tetrahydro-quinolin-5-yl or quinolin-8-yl group.

Preferred compounds of general formula I above are however those wherein $R_1$ denotes an N-methyl-benzylamino group, a piperidino group optionally substituted in the 4-position by a $C_{1-3}$-alkyl group or by a hydroxy, cyano, aminocarbonyl, methylamino or N-acetyl-methylamino group, a piperidino group substituted by two or three methyl groups, a 4-methyl-piperidino group substituted by a carboxy, methoxycarbonyl or ethoxycarbonyl group, a morpholino group optionally substituted in the 2-position by a phenyl group, a 4-oxo-pyrrolidino, 1-oxidothiomorpholino, 2,3,4,5,6,7-hexahydro-1H-azepino, 4-methyl-piperazino, 5,6,7,8-tetrahydrothiazolo[4',5':5,4]-thieno[3,2-c]-pyridino, 4,5,6,7-tetrahydro-thieno-[3,2-c]pyridino, 5,6,7,8-tetrahydro-4H-thiazolo[4,5-d]azepino, 5,6,7,8-tetrahydro-4H-thieno[2,3-d]azepino, 5,6,7,8-tetrahydrothiazolo[4',5':5,4]thieno[3,2-c]pyridino or 2-amino-5,6,7,8-tetrahydro-thiazolo[4',5':5,4]thieno[3,2-c]pyridino group, $R_2$ denotes a hydrogen atom or a methyl group and $R_3$ denotes a phenyl group optionally substituted by a chlorine atom or by a methyl, nitro, amino, phenyl or cyclohexyl group, whilst the phenyl substituent may also be substituted by a fluorine atom or by a nitro or amino group, a phenyl group disubstituted by chlorine atoms or by methyl groups, wherein the substituents may be identical or different and additionally one of the substituents may denote a nitro or amino group, a phenyl group substituted by a hydroxy, amino, methylamino, ethylamino, dimethylamino or pyrrolyl group, whilst at the same time the phenyl group is substituted by two chlorine atoms or by two $C_{1-4}$-alkyl groups, a naphthyl group optionally mono- or disubstituted by hydroxy, methoxy or dimethylamino groups, an optionally methyl-substituted indanyl, quinolyl, 1,2,3,4-tetrahydro-quinolyl, isoquinolyl, 1,2,3,4-tetrahydro-isoquinolyl, dibenzofuryl, carbazolyl or 1,2,3,4-tetrahydro-carbazolyl group, wherein an imino group may additionally be substituted by a methyl, ethyl, methoxycarbonyl, ethoxycarbonyl, hydroxycarbonylmethyl, methoxycarbonylmethyl or ethoxycarbonylmethyl group, the enantiomers and the salts thereof.

Particularly preferred compounds are the benzimidazolyl derivatives of general formula I above substituted in the 5-position, wherein $R_1$ denotes a piperidino group optionally substituted in the 4-position by a $C_{1-3}$-alkyl group, a 4-methyl-piperidino group substituted in the 2-position by a carboxy, methoxycarbonyl or ethoxycarbonyl group, or a 4-oxo-piperidino, 2,3,4,5,6,7-hexahydro-1H-azepino, 4-methyl-piperazino, 4-methyl-1,2,3,6-tetrahydropyridino, 4,5,6,7-tetrahydro-thieno[3,2-c]pyridino, 5,6,7,8-tetrahydro-4H-thiazolo[4,5-d]azepino or 5,6,7,8-tetrahydro-4H-thieno[2,3-d]azepino group, $R_2$ denotes a hydrogen atom and $R_3$ denotes a phenyl group substituted by a hydroxy, amino, methylamino, ethylamino, dimethylamino or pyrrolyl group, whilst at the same time the phenyl group is substituted by two chlorine atoms or by two tert.butyl groups, a 4-biphenylyl group, a naphthyl group substituted by a dimethylamino group, an optionally methyl-substituted 1,2,3,4-tetrahydroquinolyl, carbazolyl, 1,2,3,4-tetrahydrocarbazolyl or dibenzofuryl group, wherein an imino group may additionally be substituted by a methyl, methoxycarbonyl, ethoxycarbonyl, hydroxycarbonylmethyl, methoxycarbonylmethyl or ethoxycarbonylmethyl group, the 1-, 3-isomer mixtures thereof and the enantiomers thereof as well as the salts.

According to the invention the new compounds are obtained by the following methods:

a) Cyclising a compound of general formula

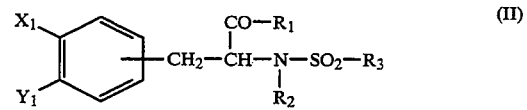

wherein

R$_1$, R$_2$ and R$_3$ are as hereinbefore defined, one of the groups X$_1$ or Y$_1$ denotes a formylamino group and the other group X$_1$ or Y$_1$ denotes an amino group.

The cyclisation is conveniently carried out in a solvent or mixture of solvents such as ethanol, isopropanol, benzene, chlorobenzene, toluene, xylene, glycol, glycol monomethylether, diethyleneglycol dimethylether, sulpholane, dimethylformamide, tetraline or in formic acid, at temperatures between 0° and 100° C., but preferably at the boiling temperature of the reaction mixture, optionally in the presence of a condensing agent such as phosphorusoxychloride, thionyl chloride, sulphuryl chloride, sulphuric acid, p-toluenesulphonic acid, methanesulphonic acid, hydrochloric acid, phosphoric acid, polyphosphoric acid, acetic anhydride or optionally in the presence of a base such as potassium ethoxide or potassium tert.butoxide. However, the cyclisation may also be carried out without a solvent and-/or condensing agent.

However, it is particularly advantageous to carry out the reaction by preparing a compound of formula II in the reaction mixture by reducing a corresponding o-nitro-amino compound, optionally in the presence of formic acid, or by acylating a corresponding o-diamino compound.

b) Reacting a compound of general formula

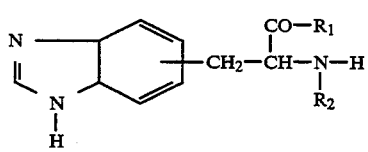

(III)

wherein

R$_1$ and R$_2$ are as hereinbefore defined, with a compound of general formula $$Z_1-SO_2-R_3 \quad (IV)$$

wherein

R$_3$ is as hereinbefore defined and Z$_1$ denotes a nucleophilic leaving group such as a halogen atom, an alkoxy, alkylthio or benzyloxy group, e.g. a chlorine or bromine atom, or a methoxy, ethoxy, methylthio, ethylthio or benzyloxy group.

The reaction is conveniently carried out in a solvent or mixture of solvents such as water, methylene chloride, chloroform, ether, tetrahydrofuran, dioxane or dimethylformamide, optionally in the presence of an inorganic or tertiary organic base, such as sodium hydroxide, potassium carbonate, triethylamine or pyridine, whilst the latter two may simultaneously serve as solvent, at temperatures between −25° and 100° C., but preferably at temperatures between −10° and 80° C.

c) Reacting a compound of general formula

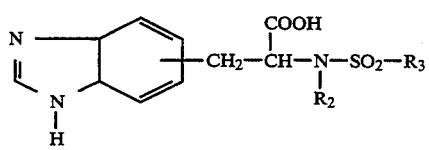

(V)

wherein

R$_2$ and R$_3$ are as hereinbefore defined, or a reactive derivative thereof, with a compound of general formula $$H-R_1 \quad (VI)$$

wherein

R$_1$ is as hereinbefore defined.

The reaction is conveniently carried out in a solvent such as methylene chloride, chloroform, carbon tetrachloride, ether, tetrahydrofuran, dioxane, benzene, toluene, acetonitrile or dimethylformamide, but particularly advantageously in an excess of the compound of general formula VI used, optionally in the presence of an acid activating agent or a dehydrating agent, e.g. in the presence of ethylchloroformate, thionyl chloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole or triphenylphosphine/carbon tetrachloride, and optionally in the presence of an inorganic base such as sodium carbonate or a tertiary organic base such as triethylamine or pyridine, which may simultaneously be used as solvent, at temperatures between −25° C. and 250° C., but preferably at temperatures between −10° C. and the boiling temperature of the solvent used.

d) In order to prepare compounds of general formula I wherein R$_3$ contains an alkylamino or dialkylamino group:

reductive amination of a compound of general formula

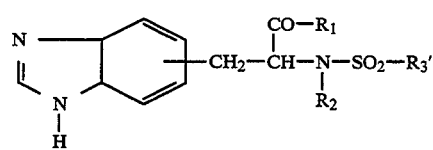

(VII)

wherein

R$_1$ and R$_2$ are as hereinbefore defined and R$_3$' denotes a phenyl group substituted by an amino or alkylamino group, which may additionally be substituted by two chlorine or bromine atoms or by two C$_{1-4}$-alkyl groups, with an alkanal having 1 to 3 carbon atoms.

The reductive amination is carried out in a suitable solvent such as methanol, ethanol, tetrahydrofuran, dioxane or acetonitrile in the presence of a suitable reducing agent such as formic acid or a suitable complex metal hydride, but preferably in the presence of sodium cyanoborohydride at a pH of 5 to 7, at temperatures between 0° and 50° C., but preferably at ambient temperature.

If according to the invention a compound of general formula I is obtained wherein R$_3$ contains an amino group, this may be converted by reaction of a corresponding furan into a corresponding compound of general formula I wherein R$_3$ contains a corresponding pyrrolyl group, or a compound of general formula I wherein R$_3$ contains a nitro group may be converted by reduction into a corresponding compound of general formula I wherein R$_3$ contains an amino group, or a compound of general formula I which contains an esterified carboxy group may be converted by hydrolysis into a corresponding carboxy compound, or a compound of general formula I wherein $R_1$ denotes a pyrrolidino, piperidino or hexamethyleneimino group substituted by an aminocarbonyl group, may be converted by dehydration into a corresponding cyano compound or a compound of general formula I wherein $R_1$ or $R_2$ or $R_1$ and $R_2$ contain a carbonyl group, may be converted by reduction into a corresponding hydroxymethylene compound or a compound of general formula I wherein $R_3$ contains a fused pyridine ring, may be converted by catalytic hydrogenation into a corresponding tetrahydro compound.

The subsequent amidation is conveniently carried out in a solvent such as methanol/glacial acetic acid, ethanol/glacial acetic acid or dioxane/propionic acid, at elevated temperatures, e.g. at temperatures between 50° and 100° C., but preferably at the boiling temperature of the reaction mixture.

The subsequent reduction of the nitro group is preferably carried out in a solvent such as water, water/ethanol, methanol, glacial acetic acid, ethyl acetate or dimethylformamide, expediently with hydrogen in the presence of a hydrogenation catalyst such as Raney nickel, platinum or palladium/charcoal, with metals such as iron, tin or zinc in the presence of an acid, with salts such as iron(II)sulphate, tin(II)-chloride, sodium sulphide, sodium hydrogen sulphite or sodium dithionite, or with hydrazine in the presence of Raney nickel, at temperatures between 0° and 80° C., but preferably at temperatures between 20° and 40° C.

The subsequent hydrolysis is preferably carried out hydrolytically in an aqueous solvent, e.g. in water, isopropanol/water, tetrahydrofuran/water or dioxane/water, in the presence of an acid such as hydrochloric acid or sulphuric acid or in the presence of an alkali metal base such as sodium hydroxide or potassium hydroxide, at temperatures between 0° and 100° C., preferably at the boiling temperature of the reaction mixture.

The subsequent dehydration is preferably carried out in a solvent such as benzene, toluene or dichlorobenzene in the presence of a dehydrating agent such as phosphorus oxychloride, thionyl chloride or phosphorus pentoxide, at temperatures between 25° and 75° C.

The subsequent reduction of the carboxy group is carried out in a suitable solvent such as methanol, ethanol, ether, tetrahydrofuran, dioxane or glacial acetic acid in the presence of catalytically activated hydrogen, e.g. hydrogen in the presence of platinum or palladium/charcoal, and optionally in the presence of an acid such as hydrochloric acid or perchloric acid or in the presence of a metal hydride such as sodium borohydride, lithium borohydride or lithium aluminium hydride, at temperatures between 0° and 100° C., preferably at temperatures between 20° and 80° C.

The subsequent catalytic hydrogenation is preferably carried out in a solvent such as water, water/ethanol, methanol, glacial acetic acid, ethyl acetate or dimethylformamide in the presence of a hydrogenation catalyst such as Raney nickel, platinum or palladium/charcoal, at temperatures between 0° and 80° C., but preferably at temperatures between 20° and 40° C.

Moreover, the compounds of general formula I obtained may be resolved into the enantiomers and/or diastereomers thereof. Cis/trans mixtures for example may be resolved into the cis- and trans-isomers and compounds having at least one optically active carbon atom may be resolved into their enantiomers.

Thus, for example, the cis/trans mixtures obtained may be separated by chromatography into their cis and trans isomers, the compounds of general formula I obtained in the form of racemates may be separated by known methods (see Allinger N. L. and Eliel E. L. in "Topics in Stereochemistry" Vol 6, Wiley Interscience, 1971) into their optical antipodes and compounds of general formula I having at least 2 asymmetric carbon atoms can be separated on the basis of their physical-chemical differences into their diastereomers by methods known per se, e.g. by chromatography and/or fractional crystallisation, and if these diastereomers are obtained in racemic form they may subsequently be separated into the enantiomers as mentioned above.

Enantiomer separation is preferably achieved by column separation on chiral phases or by recrystallisation from an optically active solvent or by reacting with optically active substances, particularly acids and their activated derivatives or alcohols, which form salts or derivatives such as esters or amides with the racemic compound, and separating the diastereomeric salt or derivative mixture obtained in this way, e.g. on the basis of different solubilities, whilst the free antipodes may be liberated from the pure diastereomeric salts or derivatives by the action of suitable agents. Particularly common optically active acids are, for example, the D and L forms of tartaric acid or dibenzoyltartaric acid, di-o-tolyl-tartaric acid, malic acid, mandelic acid, camphorsulphonic acid, glutamic acid, aspartic acid or quinic acid. An optically active alcohol might be, for example, (+)- or (−)-menthol and an optically active acyl group in amides might be, for example, (+) or (−)-menthyloxycarbonyl.

Moreover, the compounds of formula I obtained may be converted into the salts thereof, more particularly for pharmaceutical use into the physiologically acceptable salts thereof with inorganic or organic acids. Examples of suitable acids include hydrochloric acid, hydrobromic acid, sulphuric acid, phosphoric acid, fumaric acid, succinic acid, lactic acid, citric acid, tartaric acid or maleic acid.

In addition, the new compounds of formula I thus obtained, should they contain a carboxyl group, may if desired subsequently be converted into the addition salts thereof with inorganic or organic bases, more particularly for pharmaceutical use into the physiologically acceptable salts thereof. Examples of suitable bases include sodium hydroxide, potassium hydroxide, cyclohexylamine, ethanolamine, diethanolamine and triethanolamine.

The compounds of general formulae II to VII used as starting materials are known from the literature in some cases or may be obtained by methods known from the literature.

Thus, for example, a compound of general formula II is obtained by reducing a corresponding o-amino-nitro compound which is in turn obtained by trifluoroacetylation of a corresponding 4-nitrophenylalanine, reduction of the nitro group with simultaneous acetylation, nitration of the acetylated compound thus obtained, with subsequent amidation of the resulting carboxylic acid, cleaving of the trifluoroacetyl group and sulphonation of the resulting o-amino-nitro-phenylalanineamide.

A compound of general formulae III, V and VII is obtained by reduction and cyclisation of a corresponding o-amino-nitro-phenylalanineamide as mentioned above with formic acid.

As already mentioned hereinbefore, the new compounds of general formula I and the physiologically acceptable salts thereof have valuable pharmacological properties, particularly the effect of extending the thrombin time.

For example, the following compounds
A = 4-amino-N-[1-(1H-benzimidazol-5-yl-methyl)-2-(4-ethyl-piperidin-1-yl)-2-oxo-ethyl]-3,5-dichlorobenzenesulphonamide,
B = N-[1-(1H-benzimidazol-5-yl-methyl)-2-(4-ethyl-piperidin-1-yl)-2-oxo-ethyl]-3,5-dichloro-4-ethylamino-benzenesulphonamide,
C = 4-amino-N-[1-(1H-benzimidazol-5-yl-methyl)-2-(4-ethyl-piperazin-1-yl)-2-oxo-methyl]-3,5-dichloro-benzenesulphonamide,
D = N-[1-(1H-benzimidazol-5-yl-methyl)-2-(4-methyl-piperidin-1-yl)-2-oxo-ethyl]-9-methyl-1,2,3,4-tetrahydro-carbazol-6-yl-sulphonamide,
E = 4-amino-N-[1-(1H-benzimidazol-5-yl-methyl)-2-(4,5,6,7-tetrahydro-thieno[3,2-c]pyridin-5-yl)-2-oxo-ethyl]-3,5-dichloro-benzenesulphonamide,
F = 4-amino-N-[1-(1H-benzimidazol-5-yl-methyl)-2-(piperidin-4-on-1-yl)-2-oxo-ethyl]-3,5-dichlorobenzenesulphonamide,
G = N-[1-(1H-benzimidazol-5-yl-methyl)-2-(4-methyl-piperidin-1-yl)-2-oxo-ethyl]-1,2,3,4-tetrahydroquinolin-8-yl-sulphonamide,
H = 4-amino-N-[1-(1H-benzimidazol-5-yl-methyl)-2-(2,3,4,5,6,7-hexahydro-1H-azepin-1-yl)-2-oxo-ethyl]-3,5-dichloro-benzenesulphonamide
I = N-[1-(1H-benzimidazol-5-yl-methyl)-2-(4-methyl-piperid in-1-yl)-2-oxo-ethyl]-9-ethyl-carbazol-3-yl-sulphonamide
J = 4-amino-N-[1-(1H-benzimidazol-5-yl-methyl)-2-(4-methyl piperidin-1-yl)-2-oxo-ethyl]-3,5-dichlorobenzenesulphonamide
were investigated as follows for their effect on the thrombin time:
Materials:
  plasma, from human citrated blood. Test thrombin (bovine), 30 U/ml, Behring Werke, Marburg Diethylbarbiturate acetate buffer, ORWH 60/61, Behring Werke, Marburg Biomatic B10 coagulometer, Sarstedt
Method:
The thrombin time was determined using a Biomatic B10 coagulometer made by Messrs. Sarstedt.

As the test substance, 0.1 ml of human citrated plasma and 0.1 ml diethylbarbiturate buffer (DBA buffer) were added to the test strip prescribed by the manufacturer. The mixture was incubated for one minute at 37° C. The clotting reaction was started by the addition of 0.3 U test thrombin in 0.1 ml DBA buffer. The time is measured using the apparatus from the addition of the thrombin up to the clotting of the mixture.

According to the definition, a dosage-activity curve was used to determine the effective concentration of the substance, i.e. the concentration at which the thrombin time is doubled compared with the control.

The Table which follows contains the results found:

| Substance | Thrombin time (ED$_{200}$ in μM) |
|---|---|
| A | 2.5 |
| B | 1.7 |

-continued

| Substance | Thrombin time (ED$_{200}$ in μM) |
|---|---|
| C | 4.8 |
| D | 2.2 |
| E | 2.7 |
| F | 1.9 |
| G | 9.2 |
| H | 4.6 |
| I | 8.3 |
| J | 4.2 |

Moreover, no toxic side effects were observed when the compounds mentioned above were administered in doses of up to 30 mg/kg i.v. or 300 mg/kg p.o. The compounds are thus well tolerated.

In view of their pharmacological properties the new compounds and the physiologically acceptable salts thereof are suitable for the prevention and treatment of venous and arterial thrombotic diseases, such as for example deep leg vein thrombosis, for preventing reocclusions after bypass operations or percutaneous transluminal coronary angioplasty [PT(C)A], and occlusion in peripheral arterial diseases such as pulmonary embolism, disseminated intravascular coagulation, etc. In addition, the compounds according to the invention are suitable for antithrombotic support in thrombolytic treatment, e.g. with rt-PA or streptokinase.

The dosage required to achieve such an effect is appropriately 1 to 50 mg/kg, preferably 5 to 30 mg/kg by intravenous route and 5 to 100 mg/kg, preferably 10 to 50 mg/kg by oral route, in each case administered 1 to 3 times a day. For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water-/ethanol, water/glycerol, water/sorbitol, water/polyethyleneglycol, propyleneglycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The Examples which follow are intended to illustrate the invention:
Preparation of the starting products:

EXAMPLE I

N-Trifluoroacetyl-4-nitro-phenylalanine

A solution of 68 g (0.31 Mol) of 4-nitro-phenylalaninehydrate in 205 ml trifluoroacetic acid is slowly added dropwise to 87.5 ml (0.62 Mol) of trifluoroacetic acid anhydride. After one hours' stirring at 30° C. the mixture is poured into 150 ml of ice water and after another hour the precipitate formed is suction filtered.

Yield: 77.5 g (79% of theory), Melting point: 140°–141° C. $C_{11}H_9F_3N_2O_5$ (306.20) Calc. ×0.5 $H_2O$: C 41.92 H 3.20 N 8.89 Found: 42.15 3.20 8.86

EXAMPLE II

N-Trifluoroacetyl-4-acetylamino-phenylalanine

A mixture of 60.8 g (0.2 Mol) of N-trifluoroacetyl-4-nitro-phenylalanine, 250 ml of glacial acetic acid, 94 ml (1.0 Mol) of acetic anhydride and 10 g 10% palladium/-charcoal is hydrogenated for 5 hours at 50° C. under 5 bars of hydrogen. The mixture is then suction filtered and the filtrate is evaporated to dryness.

Yield: 63.2 g (100% of theory).

EXAMPLE III

N-Trifluoroacetyl-4-acetylamino-3-nitro-Phenylalanine 63.2 g (0.2 Mol) of N-trifluoroacetyl-4-acetylaminophenylalanine are suspended in 300 ml of glacial acetic acid and 100 ml of acetic anhydride. After the solution has been cooled to 10° C., 1.5 g (0.022 Mol) of sodium nitrite are added and then 33.14 ml (0.8 Mol) of fuming nitric acid are slowly added dropwise, during which time a solution is formed. After stirring for 2 hours at 0° C. the mixture is poured onto 1 kg of ice and extracted 3 times with 250 ml of ethyl acetate. After the organic phase has been dried the mixture is concentrated by evaporation, the resulting residue is mixed twice with a mixture of 150 ml of ethyl acetate and 150 ml of toluene and evaporated down again. The residue obtained this time is combined with 100 ml of ethyl acetate cooled to −10° C., suction filtered and washed again with ethyl acetate cooled to −10° C.

Yield: 50 g (69% of theory), Melting point: 180°–185° C.

EXAMPLE IV

N-Trifluoroacetyl-4-acetylamino-3-nitro-phenylalanyl-(4-methyl-piperidine)

A solution of 5.3 g (14.6 mMol) of N-trifluoroacetyl-4-acetylamino-3-nitro-phenylalanine in 20 ml of absolute dimethylformamide is combined with 2.4 g (14.6 mMol) of carbonyldiimidazole with stirring at 20° C. After stirring for 1 hour at 20° C., 8.4 ml (0.069 Mol) of 4-methyl-piperidine are added and the mixture is stirred for 2 hours at 20° C. It is then evaporated to dryness, the residue is taken up in 500 ml of ethyl acetate and extracted 3 times with 2N hydrochloric acid. After the organic phase has been washed with saturated saline solution it is dried and evaporated down once more. The residue obtained is digested in ether and suction filtered.

Yield: 5.0 g (77.0% of theory), Melting point: 174°–178° C. $C_{19}H_{23}F_3N_4O_5$ (444.40) Calculated: C 51.35 H 5.22 N 12.61 Found: 51.09 5.10 12.40

EXAMPLE V

4-Amino-3-nitro-phenylalanyl-(4-methyl-piperidine)

To a suspension of 4.85 g (10.9 mMol) of N-trifluoroacetyl-4-acetylamino-3-nitro-phenylalanyl-(4-methyl-piperidine) in 10 ml of ethanol 28.0 ml of 1N sodium hydroxide solution are added dropwise at 20° C. After 3 hours' stirring at 50° C. the mixture is cooled, then after another 2 hours it is suction filtered and washed with a little ice water.

Yield: 3.1 g (93% of theory), Melting point: 160°–161° C. $C_{15}H_{22}N_4O_3$ (306.36) Calculated: C 58.81 H 7.21 N 18.29 Found: 58.63 7.03 18.34

EXAMPLE VI

4-Amino-N-[1-((4-amino-3-nitro-phenyl)-methyl)-2-(4-methyl-piperidin-1-yl)-2-oxo-ethyl]-3,5-dichlorobenzenesulphonamide 3.06 g (10 mMol) of 4-amino-3-nitro-phenylalanyl-(4-methyl-piperidine) are dissolved in 100 ml of methylene chloride and combined with 2.8 ml (20 mMol) of triethylamine. Then at ambient temperature 3.1 g (12 mMol) of 4-amino-3,5-dichloro-benzenesulphonic acid chloride in 20 ml of methylene chloride is slowly added dropwise. After 2 hours the precipitate is suction filtered, washed with methylene chloride and dried at 70° C. For further purification the precipitate is suspended in 100 ml of ethanol, decocted and after cooling suction filtered again.

Yield: 4.6 g (86.8% of theory), Melting point: 236°–237° C. $C_{21}H_{25}Cl_2N_5O_5S$ (530.43) Calculated: C 47.55 H 4.75 N 13.20 Found: 47.55 4.82 13.40

The following compounds are obtained analogously:

N-[1-((4-amino-3-nitro-phenyl)-methyl)-2-(4-methyl-piperidin-1-yl)-2-oxo-ethyl]-2,5-dimethyl-benzene sulphonamide N-[1-((4-amino-3-nitro-phenyl)-methyl)-2-(4-methyl-piperidin-1-yl)-2-oxo-ethyl]-6,7-dimethoxy-naphthalene-2-sulphonamide N-[1-((4-amino-3-nitro-phenyl)-methyl)-2-(4-methyl-piperidin-1-yl)-2-oxo-ethyl]-5-dimethylaminonaphthalene-1-sulphonamide N-[1-((4-amino-3-nitro-phenyl)-methyl)-2-(4-methyl-piperidin-1-yl)-2-oxo-ethyl]-2′-fluoro-4-biphenylsulphonamide 4-amino-N-[1-((4-amino-3-nitro-phenyl)-methyl)-2-(4,4-ethylenedioxy-piperidin-1-yl)-2-oxo-ethyl]-3,5-dichlorobenzenesulphonamide 4-amino-N-[1-((4-amino-3-nitro-phenyl)-methyl)-2-(5,6,7,8-tetrahydro-4H-thiazolo[5,4-d]azepin-6-yl)-2-oxo-ethyl]-3,5-dichloro-benzenesulphonamide 4-amino-N-[1-((4-amino-3-nitro-phenyl)-methyl)-2-(5,6,7,8-tetrahydro-4H-thieno[2,3-d]azepin-6-yl)-2-oxoethyl]-3,5-dichloro-benzenesulphonamide 4-amino-N-[1-((4-amino-3-nitro-phenyl)-methyl)-2-(4,4-ethylenedioxy-piperidin-1-yl)-2-oxo-ethyl]-3,5-dichlorobenzenesulphonamide 4-amino-N-[1-((4-amino-3-nitro-phenyl)-methyl)-2-(1-oxido-thiomorpholin-4-yl)-2-oxo-ethyl]-3,5-dichlorobenzenesulphonamide 4-amino-N-[1-((4-amino-3-nitro-phenyl)-methyl)-2-(4-n-propyl-piperidin-1-yl)-2-oxo-ethyl]-3,5-dichlorobenzenesulphonamide N-[1-((4-amino-3-nitro-phenyl)-methyl)-2-(4-methyl-piperidin-1-yl)-2-oxo-ethyl]-naphthalene-2-sulphonamide N-[1-((4-amino-3-nitro-phenyl)-methyl)-2-(4-methyl-piperidin-1-yl)-2-oxo-ethyl]-4-biphenylyl-sulphonamide N-[1-((4-amino-3-nitro-phenyl)-methyl)-2-(4-methypiperidin-1-yl)-2-oxo-ethyl]-3′-nitro-4-biphenylylsulphonamide 4-cyclohexyl-N-[1-((4-amino-3-nitro-phenyl)-methyl)-2-(4-methyl-piperidin-1-yl)-2-oxo-ethyl]benzenesulphonamide

EXAMPLE VII 1-(1H-Benzimidazol-5-yl-methyl)-2-[(4-methyl-piperidin-1-yl)]-2-oxo-ethylamine 20 g (0.065 Mol) of 4-amino-3-nitro-phenylalanyl-(4-methyl-piperidine) are dissolved in 250 ml of formic acid, mixed with 2.0 g of palladium/charcoal and hydrogenated in the autoclave for 1 hour at 5 bar and 25° C. The catalyst is filtered off and the filtrate is concentrated by rotary evaporation in vacuo and the residue is taken up in 50 ml of water. It is then made alkaline with 6N sodium hydroxide solution and extracted with methylene chloride. The combined organic extracts are dried over sodium sulphate and evaporated down.

Yield: 15.2 g (82% of theory), Melting point: 160°–162° C. $C_{16}H_{22}N_4O \times 0.6$ $H_2O$ (297.15) Calc. $\times 0.6$ $H_2O$: C 64.67 H 7.87 N 18.85 Found: 64.88 7.76 18.92

EXAMPLE VIII

N-(4-Amino-3,5-dichloro-benzenesulphamoyl)-4-amino-3-nitro-phenylalanine 10 g (0.0275 Mol) of N-trifluoroacetyl-4-acetylamino-3-nitro-phenylalanine are dissolved in 20 ml of ethanol and stirred with 82 ml of 1N sodium hydroxide solution at ambient temperature for 3 hours. Then a solution of 10.7 g (0.041 Mol) of 4-amino-3,5-dichlorobenzenesulphonic acid chloride, dissolved in 30 ml of acetone, is added dropwise, whilst the pH is maintained at about 10.7 by the batchwise addition of sodium hydroxide solution. After 12 hours' stirring at ambient temperature the organic solvent is eliminated in vacuo and the aqueous solution is acidified to pH 4.5. The precipitate formed is stirred for 2 hours and then suction filtered, washed with water and dried.

Yield: 10.7 g (86.6% of theory), Melting point: 204°–208° C. (decomp.) $C_{15}H_{14}Cl_2N_4O_6S$ (449.26) Calc.: C 40.10 H 3.14 N 12.47 S 7.13 Cl 15.78 Found: 39.79 3.03 12.58 7.44 16.38

EXAMPLE IX

2-(4-Amino-3,5-dichloro-benzenesulphamoyl)-3-(1H-benzimidazol-5-yl)-propionic acid To a mixture of 47.0 g (0.105 Mol) of N-(4-amino-3,5-dichloro-benzenesulphonyl)-4-amino-3-nitro-phenylalanine and 1000 ml of formic acid are added 15 g of palladium/charcoal. The reaction mixture thus obtained is hydrogenated for 3.5 hours at 50°–60° C. under a hydrogen pressure of 5 bar. Then the catalyst is suction filtered and the filtrate is evaporated down in vacuo. The product obtained is further purified by esterifying with 40 ml of thionylchloride dissolved in 800 ml of ethanol, and then chromatographed over a silica gel column (eluant: ethyl acetate/methanol/ammonia 9:1:0.1). 10.5 g of the ester thus obtained are dissolved in 150 ml of ethanol and saponified by means of 80 ml of 1N sodium hydroxide solution and then the desired product is precipitated by neutralising with water/hydrochloric acid and washed with ethanol.

Yield: 9.6 g (97% of theory), Melting point: from 190° C. (decomp.) $C_{16}H_{14}Cl_2N_4O_4S$ (429.28) Calc.: C 44.77 H 3.29 N 13.05 S 7.47 Cl 16.52 Found: 44.97 3.22 12.85 7.40 16.00

Preparation of the end products:

EXAMPLE 1

4-Amino-N-[1-(1H-benzimidazol-5-yl-methyl)-2-(4-methyl-piperidin-1-yl)-2-oxo-ethyl]-3,5-dichloro-benzenesulphonamide 1.06 g (2 mMol) of 4-amino-N-[1-((4-amino-3-nitrophenyl)methyl)-2-(4-methyl-piperidin-1-yl)-2-oxo-ethyl]-3,5-dichloro-benzenesulphonamide are suspended in 20 ml of formic acid and hydrogenated, with the addition of 0.1 g palladium/charcoal, in an autoclave under a hydrogen pressure of 5 bar at ambient temperature for 80 minutes. Then the catalyst is filtered off and the filtrate is heated to 50° C. for 2 hours. It is then concentrated by evaporation, mixed with 30 ml of water, made alkaline with concentrated ammonia and extracted twice with ethyl acetate. The organic phase is washed twice with water, dried over magnesium sulphate and evaporated down. The residue obtained is purified on a silica gel column (ethyl acetate/methanol/ammonia=95:5:0.5). After evaporation the residue is recrystallised from isopropanol.

Yield: 600 mg (59% of theory), Melting point: 233°–235° C. $C_{22}H_{25}Cl_2N_5O_3S$ (510.45) Calc.: C 51.87 H 4.75 N 13.75 S 6.29 Cl 13.92 Found: 51.61 4.93 13.39 6.27 14.43

EXAMPLE 2

N-[1-(1H-Benzimidazol-5-yl-methyl)-2-(4-methyl-piperidin-1-yl)-2-oxo-ethyl]-9-methyl-1,2,3,4-tetrahydro-carbazol-6-sulphonamide To a solution of 1 g (0.0034 Mol) of 1-(1H-benzimidazol-5-yl-methyl)-2-(4-methyl-piperidin-1-yl)-2-oxoethylamine and 1.1 g (0.011 Mol) of triethylamine in 30 ml of chloroform are added dropwise, at ambient temperature and with stirring, 0.96 g (0.0034 Mol) of 9-methyl-1,2,3,4-tetrahydro-carbazol-6-sulphonic acid chloride dissolved in 10 ml of chloroform. After 12 hours' stirring the mixture is evaporated down in vacuo and the residue obtained is chromatographed over a silica gel column (eluant: ethyl acetate/methanol=9:1). The eluate having an $R_f$ value of 0.3 is collected and evaporated down in vacuo.

Yield: 0.9 g (50% of theory), Melting point: 190°–192° C. (decomp.) $C_{29}H_{35}N_4O_3S$ (533.67) Calc.: C 65.26 H 6.60 N 13.12 S 6.00 Found: 64.96 6.64 12.94 5.97

EXAMPLE 3

N-[1-(1H-Benzimidazol-5-yl-methyl)-2-(4-methyl-piperidin-1-yl)-2-oxo-ethyl]-2,5-dimethylbenzenesulphonamide Prepared from 4-amino-N-[1-((4-amino-3-nitrophenyl)methyl)-2-(4-methyl-piperidin-1-Yl)-2-oxo-ethyl]-3,5-dimethyl-benzenesulphonamide analogously to Example 1.

Yield: 64% of theory, Melting point: 144°–146° C. $C_{24}H_{30}N_4O_3S \times H_2O$ (472.60) Calculated: C 60.99 H 6.83 N 11.87 Found: 61.22 6.97 11.43

EXAMPLE 4

N-[1-(1H-Benzimidazol-5-yl-methyl)-2-(4-methyl-piperidin-1-yl)-2-oxo-ethyl]-6,7-dimethoxy-naphthalene-2-sulphonamide Prepared from 4-amino-N-[1-((4-amino-3-nitrophenyl)methyl)-2-(4-methyl-piperidin-1-yl)-2-oxo-ethyl]-6,7-dimethoxy-naphthalene-2-sulphonamide analogously to Example 1.

Yield: 36.6% of theory, Melting point: foam $C_{28}H_{32}N_4O_5S$ (536.66) Calculated: C 62.67 H 6.01 N 10.44 S 5.97 Found: 62.40 6.17 10.05 5.54

EXAMPLE 5

N-[1-(1H-Benzimidazol-5-yl-methyl)-2-(4-methyl-piperidin-1-yl)-2-oxo-ethyl]-5-dimethylaminonaphthalene-1-sulphonamide Prepared from 4-amino-N-[1-((4-amino-3-nitrophenyl)methyl)-2-(4-methyl-piperidin-1-yl)-2-oxo-ethyl]-5-dimethylamino-naphthalene-1-sulphonamide analogously to Example 1.

Yield: 66.8% of theory, Melting point: from 210° C. (decomp.) $C_{28}H_{33}N_5O_3S$ (519.67) Calculated: C 64.72 H 6.40 N 13.48 S 6.17 Found: 64.56 6.37 13.69 5.96

EXAMPLE 6

N-[1-(1H-Benzimidazol-5-yl-methyl)-2-(4-ethyl-piperidin-1-yl)-2-oxo-ethyl]-3,5-dichloro-4-dimethylaminobenzenesulphonamide To a mixture of 0.7 g (0.0078 Mol) of paraformaldehyde and 20 ml of formic acid, heated to 110° C., are added in batches 1.6 g (0.003 Mol) of 4-amino-N-[1-(1H-benzimidazol-5-yl-methyl)-2-(4-ethyl-piperidin-1-yl)-2-oxo-ethyl]-3,5-dichloro-benzenesulphonamide. The mixture is then heated to 120° C. for a further hour. It is cooled, evaporated down in vacuo and the residue obtained is chromatographed over a silica gel column (eluant: ethyl acetate/methanol=19:1). The fractions having an $R_f$ value of 0.43 are collected and evaporated down in vacuo.

Yield: 19.3% of theory, Melting point: from 86° C. (decomp.) $C_{25}H_{31}Cl_2N_5O_3S$ (552.53) Calc.$\times H_2O$: C 52.62 H 5.62 N 12.27 S 5.61 Found: 52.46 5.45 12.23 5.64

EXAMPLE 7

N-[1-(1H-Benzimidazol-5-yl-methyl)-2-(4-methyl-piperidin-1-yl)-2-oxo-ethyl]-3,5-dichloro-4-dimethylamino-benzenesulphonamide Prepared from 4-amino-N-[1-(1H-benzimidazol-5-yl-methyl)-2-(4-methyl-piperidin-1-yl)-2-oxo-ethyl]-3,5-dichloro-benzenesulphonamide and paraformaldehyde analogously to Example 6.

Yield: 18.0% of theory, Melting point: from 100° C. (decomp.) $C_{24}H_{29}Cl_2N_5O_3S$ (538.50) Calc.: C 53.53 H 5.42 N 13.00 S 5.95 Cl 13.16 Found: 53.77 5.38 12.85 6.03 13.74

EXAMPLE 8

N-[1-(1H-Benzimidazol-5-yl-methyl)-2-(4-ethyl-piperidin-1-yl)-2-oxo-ethyl]-3,5-dichloro-4-ethylaminobenzenesulphonamide Prepared from 4-amino-N-[1-(1H-benzimidazol-5-yl-methyl)-2-(4-methyl-piperidin-1-yl)-2-oxo-ethyl]-3,5-dichloro-benzenesulphonamide and acetaldehyde analogously to Example 6.

Yield: 8.6% of theory, Melting point: from 140° C. (decomp.) $C_{25}H_{31}Cl_2N_5O_3S$ (552.53) Calculated: C 54.34 H 5.65 N 12.67 Found: 54.09 5.46 12.44

EXAMPLE 9

N-[1-(1H-Benzimidazol-5-yl-methyl)-2-(4-methyl-piperidin-1-yl)-2-oxo-ethyl]-3,5-dichloro-4-pyrrolylbenzenesulphonamide 1.1 g (0.00215 Mol) of 4-amino-N-[1-(1H-benzimidazol-5-yl-methyl)-2-(4-methyl-piperidin-1-yl)-2-oxo-ethyl]-3,5-dichloro-benzenesulphonamide are refluxed for 4 hours with 0.4 g (0.03 Mol) of 2,5-dimethoxy-tetrahydrofuran in 3 ml of glacial acetic acid and 3 ml of methanol. The mixture is then evaporated to dryness in vacuo and the residue obtained is chromatographed over a silica gel column (eluant: ethyl acetate/methanol=9:1). The fractions having an $R_f$ value of 0.4 are collected and evaporated down in vacuo.

Yield: 25.0% of theory, Melting point: from 100° C. (decomp.) $C_{26}H_{27}Cl_2N_5O_3S$ (560.51) Calc.: C 55.71 H 4.85 N 12.49 S 5.71 Cl 12.65 Found: 55.95 5.12 11.91 5.76 12.48

EXAMPLE 10

N-[1-(1H-Benzimidazol-5-yl-methyl)-2-(4-methyl-phenyl)methyl-piperidin-1-yl)-2-oxo-ethyl]-2'-fluoro-4-biphenylylsulphonamide Prepared from 4-amino-N-[1-((4-amino-3-nitrophenyl)methyl)-2-(4-methyl-piperidin-1-yl)-2-oxo-ethyl]-2'-fluoro-4-biphenylyl-sulphonamide analogously to Example 1.

Yield: 67.0% of theory, Melting point: from 195° C. (decomp.) $C_{28}H_{29}FN_4O_3S$ (520.63) Calculated: C 64.60 H 5.61 N 10.76 S 6.16 Found: 64.20 5.44 11.04 6.28

EXAMPLE 11

N-[1-(1H-Benzimidazol-5-yl-methyl)-2-(4-methyl-piperidin-1-yl)-2-oxo-ethyl]-dibenzofuran-2-sulphonamide Prepared from 1-(1H-benzimidazol-5-yl-methyl)-2-(4-methyl-piperidin-1-yl)-2-oxo-ethylamine and dibenzofuran-2-sulphonic acid chloride analogously to Example 2.

Yield: 39.0% of theory, Melting point: from 85° C. (decomp.) $C_{28}H_{28}N_4O_4S$ (516.62) Calc.$\times H_2O$: C 62.90 H 5.65 N 10.48 S 5.99 Found: 62.70 5.82 9.94 6.37

EXAMPLE 12

N-[1-(1H-Benzimidazol-5-yl-methyl)-2-(4-methyl-piperidin-1-yl)-2-oxo-ethyl]-9-ethyl-carbazol-3sulphonamide Prepared from 1-(1H-benzimidazol-5-yl-methyl)-2-(4-methyl-piperidin-1-yl)-2-oxo-ethylamine and 9-ethyl-carbazol-3-sulphonic acid chloride analogously to Example 2.

Yield: 54.0% of theory, Melting point: from 100° C. (decomp.) $C_{20}H_{33}N_5O_3S$ (543.69) Calc.$\times H_2O$: C 64.15 H 6.27 N 12.46 S 5.70 Found: 64.04 6.10 11.60 5.76

EXAMPLE 13

Ethyl [3-[[1-(1H-benzimidazol-5-yl-methyl)-2-(4-methyl-piperidin-1-yl)-2-oxo-ethyl]sulphamoyl]-carbazol-9-yl-acetate Prepared from 1-(1H-benzimidazol-5-yl-methyl)-2-(4-methyl-piperidin-1-yl)-2-oxo-ethylamine and 9-ethoxycarbonylmethyl-carbazol-3-sulphonic acid chloride analogously to Example 2.

Yield: 56.0% of theory, Melting point: from 110° C. (decomp.) $C_{32}H_{35}N_5O_5S$ (601.73) Calculated: C 63.87 H 5.86 N 11.63 S 5.32 Found: 63.62 6.04 11.42 5.62

EXAMPLE 14

N-[1-(1H-Benzimidazol-5-yl-methyl)-2-(4-methyl-piperidin-1-yl)-2-oxo-ethyl]-8-hydroxy-naphthalene-1-sulphonamide Prepared from 1-(1H-benzimidazol-5-yl-methyl)-2-(4-methyl-piperidin-1-yl)-2-oxo-ethylamine and 1,8naphthalene sultone by heating to 100° C. for 30 minutes and subsequently heating to 140° C. for 20 minutes. After cooling, the product obtained is purified over a silica gel column (eluant: ethyl acetate/methanol=9:1).

Yield: 20.0% of theory, Melting point: 240°-242° C. $C_{26}H_{28}N_4O_4S$ (492.60) Calculated: C 63.39 H 5.72 N 11.37 S 6.50 Found: 63.27 5.64 11.19 6.33

EXAMPLE 15

4-Amino-N-[1-(1H-benzimidazol-5-yl-methyl)-2-(4-ethyl-piperidin-1-yl)-2-oxo-ethyl]-3,5-dichlorobenzenesulphonamide 1.4 g (0.003 Mol) of 2-(4-amino-3,5-dichlorobenzensulphamoyl)-3-(1H-benzimidazol-5-yl)-propionic acid, 0.45 g (0.003 Mol) of 4-ethyl-piperidinehydrochloride, 0.405 g (0.003 Mol) of 1-hydroxy-1H-benzotriazole and 1 g (0.009 Mol) of N-ethyl-morpholine are dissolved in 15 ml of dimethylformamide, cooled to 0° C. and finally mixed with 0.72 g (0.0035 Mol) of N,N'-dicyclohexyl-carbodiimide. After stirring for 18 hours the dicyclohexylurea precipitated is suction filtered off and the filtrate is evaporated down in vacuo. The residue obtained is chromatographed over a silica gel column (eluant: methylene chloride/ethanol=9:1) and the fractions having an $R_f$ value of 0.68 are collected and evaporated down in vacuo.

Yield: 70.0% of theory, Melting point: from 95° C. (decomp.) $C_{23}H_{27}Cl_2N_5O_3S$ (524.47) Calc.: C 52.67 H 5.18 N 13.35 S 6.11 Cl 13.52 Found: 52.68 5.23 12.90 6.04 13.40

EXAMPLE 16

4-Amino-N-[1-(1H-benzimidazol-5-yl-methyl)-2-(2,4,6-trimethyl-piperidin-1-yl)-2-oxo-ethyl]-3,5-dichlorobenzenesulphonamide Prepared from 2-(4-amino-3,5-dichlorobenzenesulphamoyl)-3-(1H-benzimidazol-5-yl)-propionic acid and 2,4,6-trimethyl-piperidine analogously to Example 15.

Yield: 10.0% of theory, Melting point: from 90° C. (decomp.) $C_{24}H_{29}Cl_2N_5O_3S$ (538.50) Calc.: C 53.53 H 5.42 N 13.00 S 5.95 Cl 13.16 Found: 53.16 5.69 12.86 6.12 12.95

EXAMPLE 17

4-Amino-N-[1-(1H-benzimidazol-5-yl-methyl)-2-(N-benzylmethylamino)-2-oxo-ethyl]-3,5-dichlorobenzenesulphonamide Prepared from 2-(4-amino-3,5-dichlorobenzenesulphamoyl)-3-(1H-benzimidazol-5-yl)-propionic acid and N-benzyl-methylamine analogously to Example 15.

Yield: 10.0% of theory, Melting point: from 80° C. (decomp.) $C_{24}H_{23}Cl_2N_5O_3S$ (532.45) Calc.: C 54.13 H 4.35 N 13.15 S 6.02 Cl 13.31 Found: 54.45 4.27 13.08 5.86 12.28

EXAMPLE 18

4-Amino-N-[1-(1H-benzimidazol-5-yl-methyl)-2-(piperidin-1-yl)-2-oxo-ethyl]-3,5-dichloro-benzenesulphonamide Prepared from 2-(4-amino-3,5-dichlorobenzenesulphamoyl)-3-(1H-benzimidazol-5-yl)-propionic acid and piperidine analogously to Example 15.

Yield: 67.0% of theory, Melting point: 272°–274° C. (sintering from 245° C.) $C_{21}H_{23}Cl_2N_5O_3S$ (496.42) Calc.: C 50.81 H 4.66 N 14.10 S 6.45 Cl 14.28 Found: 50.66 4.52 14.09 6.60 14.18

EXAMPLE 19

4-Amino-N-[1-(1H-benzimidazol-5-yl-methyl)-2-(N-methy-lindan-1-yl-amino)-2-oxo-ethyl]-3,5-dichlorobenzenesulphonamide Prepared from 2-(4-amino-3,5-dichlorobenzenesulphamoyl)-3-(1H-benzimidazol-5-yl)-propionic acid and N-methyl-indan-1-yl-amine analogously to Example 15.

Yield: 23.0% of theory, Melting point: 156° C. $C_{26}H_{25}OCl_2N_5O_3S$ (558.49) Calculated: C 55.92 H 4.51 N 12.54 Found: 56.08 4.63 12.84

Example 20

N-[1-(1H-Benzimidazol-5-yl-methyl)-2-(4-methyl-piperidin-1-yl)-2-oxo-ethyl]-4-chloro-3-nitrobenzenesulphonamide Prepared from 1-(1H-benzimidazol-5-yl-methyl)-2-(4-methyl-piperidin-1-yl)-2-oxo-ethylamine and 4-chloro-3-nitro-benzenesulphonic acid chloride analogously to Example 2.

Yield: 31.0% of theory, Melting point: 110° C. (decomp.) $C_{22}H_{24}ClN_5O_5S$ (505.98) Calc.: C 52.22 H 4.78 N 13.84 S 6.33 Cl 7.00 Found: 52.22 4.99 13.56 6.20 7.08

EXAMPLE 21

N-[1-(1H-Benzimidazol-5-yl-methyl)-2-(4-methyl-piperidin-1-yl)-2-oxo-ethyl]-2-nitro-benzenesulphonamide Prepared from 1-(1H-benzimidazol-5-yl-methyl)-2-(4-methyl-piperidin-1-yl)-2-oxo-ethylamine and 2-nitro-benzenesulphonic acid chloride analogously to Example 2.

Yield: 57.0% of theory, Melting point: 125° C. $C_{22}H_{25}N_5O_5S$ (471.54) Calculated: C 56.04 H 5.34 N 14.85 Found: 56.19 5.56 14.39

EXAMPLE 22

3-Amino-N-[1-(1H-benzimidazol-5-yl-methyl)-2-(4-methyl-piperidin-1-yl)-2-oxo-ethyl]-4-chlorobenzenesulphonamide 5 g (0.01 Mol) of N-[1-(1H-benzimidazol-5-yl-methyl)-2-(4-methyl-piperidin-1-yl)-2-oxo-ethyl]-4-chloro-3-nitrobenzenesulphonamide are dissolved in 50 ml of methanol and hydrogenated in the presence of 1 g of platinum/charcoal under a hydrogen pressure of 3 bar at ambient temperature. Then the catalyst is suction filtered, the filtrate is evaporated down, the residue is triturated with ether and suction filtered.

Yield: 4.5 g (94.5% of theory), Melting point: from 140° C. (decomp.) $C_{22}H_{26}ClN_5O_3S$ (467.00) Calc.×-$H_2O$: C 53.48 H 5.71 N 14.71 S 6.48 Found: 53.60 5.46 14.48 6.45

EXAMPLE 23

2-Amino-N-[1-(1H-benzimidazol-5-yl-methyl)-2-(4-methyl-piperidin-1-yl)-2-oxo-ethyl]-benzenesulphonamide Prepared from N-[1-(1H-benzimidazol-5-yl-methyl)-2-(4-methyl-piperidin-1-yl)-2-oxo-ethyl]-2-nitrobenzenesulphonamide by catalytic hydrogenation analogously to Example 22.

Yield: 29.5% of theory, Melting point: from 126° C. (decomp.) $C_{22}H_{27}N_5O_3S$ (441.56) Calculated: C 59.84 H 6.16 N 15.86 Found: 58.18 6.36 15.61

EXAMPLE 24

[3-[[1-(1H-Benzimidazol-5-yl-methyl)-2-(4-methyl-piperidin-1-yl)-2-oxo-ethyl]sulphamoyl]-carbazol-9-yl]-acetic acid To a solution of 0.6 g (0.001 Mol) of ethyl [3-[[1-(1H-benzimidazol-5-yl-methyl)-2-(4-methyl-piperidin-1-yl)-2-oxo-ethyl]sulphamoyl]-carbazol-9-yl]-acetate in 5 ml of dioxane and 5 ml of methanol are added dropwise 4 ml of 1N sodium hydroxide solution and the mixture is stirred at 20° C. for one hour. It is then diluted with 20 ml of water and mixed with 4 ml of 1N hydrochloric acid. The organic solvent is eliminated in vacuo, the product precipitated is suction filtered, washed with water and dried.

Yield: 0.5 g (87.0% of theory), Melting point: 220° C. (decomp.) $C_{30}H_{31}N_5O_5S$ (573.68) Calculated: C 62.81 H 5.44 N 12.20 S 5.58 Found: 62.66 5.57 11.98 5.24

EXAMPLE 25

4-Amino-N-[1-(1H-benzimidazol-5-yl-methyl)-2-(piperidin-4-on-1-yl)-2-oxo-ethyl]-3,5-dichloro-benzenesulphonamide Prepared from 4-amino-N-[1-((4-amino-3-nitro-phenyl)methyl]-2-(piperidin-4,4-ethylendioxy-1-yl)-2-oxoethyl]-3,5-dichloro-benzenesulphonamide and cyclising with formic acid in the presence of palladium/charcoal analogously to Example 1.

Yield: 81% of theory, Melting point: 235°-237° C. (decomp.) $C_{21}H_{21}Cl_2N_5O_4S$ (510.40) Calc.: C 49.42 H 4.15 N 13.72 S 6.28 Cl 13.89 Found: 49.59 4.42 13.44 6.44 14.07

EXAMPLE 26

4-Amino-N-[1-(1H-benzimidazol-5-yl-methyl)-2-(5,6,7,8-tetrahydro-4H-thiazolo[4,5-d]azepin-6-yl)-2-oxo-ethyl]-3,5-dichloro-benzenesulphonamide Prepared from 4-amino-N-[1-((4-amino-3-nitro-phenyl)methyl]-2-(5,6,7,8-tetrahydro-4H-thiazolo[4,5-d]azepin-6-yl)-2-oxo-ethyl]-3,5-dichloro-benzenesulphonamide and cyclising with formic acid in the presence of palladium/charcoal analogously to Example 1.

Yield: 44% of theory, Melting point: 156°-159° C. $C_{23}H_{22}Cl_2N_6O_3S$ (565.50) Calc.: C 48.85 H 3.92 N 14.86 S 11.34 Cl 12.54 Found: 48.66 4.38 14.58 11.54 12.67

EXAMPLE 27

4-Amino-N-[1-(1H-benzimidazol-5-yl-methyl)-2-(5,6,7,8-tetrahydro-4H-thieno[2,3-d]azepin-6-yl)-2-oxo-ethyl]-3,5-dichloro-benzenesulphonamide Prepared from 4-amino-N-[1-((4-amino-3-nitro-phenyl)methyl]-2-(5,6,7,8-tetrahydro-4H-thieno[2,3-d]azepin-6-yl)-2-oxo-ethyl]-3,5-dichloro-benzenesulphonamide and cyclising with formic acid in the presence of palladium/charcoal analogously to Example 1.

Yield: 50% of theory, Melting point: 143°-146° C. $C_{24}H_{23}Cl_2N_5O_3S_2$ (564.52) Calc.: C 51.07 H 4.11 N 12.41 S 11.36 Cl 12.56 Found: 50.92 4.47 12.46 11.13 12.88

EXAMPLE 28

N-[1-(1H-Benzimidazol-5-yl-methyl)-2-(4-methyl-piperidin-1-yl)-2-oxo-ethyl]-3,5-di-tert.butyl-4-hydroxy-benzenesulphonamide Prepared from N-[1-((4-amino-3-nitro-phenyl)methyl]-2-(4-methyl-piperidin-1-yl)-2-oxo-ethyl]-3,5-di-tert.butyl-4-hydroxy-benzenesulphonamide and cyclising with formic acid in the presence of palladium/charcoal analogously to Example 1.

Yield: 48.6% of theory, Melting point: 200°-202° C. $C_{30}H_{42}N_4O_4S$ (554.76) Calculated: C 64.95 H 7.63 N 10.10 S 5.78 Found: 64.63 7.96 9.92 5.63

EXAMPLE 29

4-Amino-N-[1-(1H-benzimidazol-5-yl-methyl)-2-(1-oxidothiomorpholin-4-yl)-2-oxo-ethyl]-3,5-dichlorobenzenesulphonamide Prepared from 4-amino-N-[1-((4-amino-3-nitro-phenyl)methyl]-2-(1-oxido-thiomorpholin-4-yl)-2-oxo-ethyl]-3,5-dichloro-benzenesulphonamide and cyclising with formic acid in the presence of palladium/charcoal analogously to Example 1.

Yield: 58% of theory, Melting point: 260°-263° C. $C_{20}H_{21}Cl_2N_5O_4S_2$ (530.46) Calc.: C 45.29 H 3.99 N 13.20 S 12.09 Cl 13.37 Found: 44.98 4.06 12.99 12.00 13.08

EXAMPLE 30

4-Amino-N-[1-(1H-benzimidazol-5-yl-methyl)-2-(4-propylpiperidin-1-yl)-2-oxo-ethyl]-3,5-dichlorobenzenesulphonamide Prepared from 4-amino-N-[1-((4-amino-3-nitro-phenyl)methyl]-2-(4-propyl-piperidin-1-yl)-2-oxo-ethyl]-3,5-dichloro-benzenesulphonamide and cyclising with formic acid in the presence of palladium/charcoal analogously to Example 1.

Yield: 46% of theory, Melting point: 173° C. $C_{24}H_{29}Cl_2N_5O_3S$ (538.50) Calc.: C 53.53 H 5.43 N 13.01 S 5.95 Cl 13.17 Found: 53.47 5.71 12.60 6.06 12.74

EXAMPLE 31

N-[1-(1H-Benzimidazol-5-yl-methyl)-2-(4-methyl-piperidin-1-yl)-2-oxo-ethyl]-naphthalene-2-sulphonamide Prepared from N-[1-((4-amino-3-nitro-phenyl)-methyl]-2-(4-methyl-piperidin-1-yl)-2-oxo-ethyl]-naphthalene-2sulphonamide and cyclising with formic acid in the presence of palladium/charcoal analogously to Example 1.

Yield: 40% of theory, Melting point: 130°-134° C. $C_{26}H_{28}N_4O_3S$ (476.60) Calculated: C 65.52 H 5.92 N 11.76 S 6.73 Found: 65.49 6.02 11.47 6.89

EXAMPLE 32

N-[1-(1H-Benzimidazol-5-yl-methyl)-2-(4-methyl-piperidin-1-yl)-2-oxo-ethyl]-4-biphenylyl-sulphonamide Prepared from N-[1-((4-amino-3-nitro-phenyl)-methyl]-2-(4-methyl-piperidin-1-yl)-2-oxo-ethyl]-4-biphenylylsulphonamide and cyclising with formic acid in the presence of palladium/charcoal analogously to Example 1.

Yield: 63% of theory, Melting point: 127°-130° C. $C_{28}H_{30}N_4O_3S$ (502.64) Calculated: C 66.91 H 6.02 N 11.15 S 6.38 Found: 66.70 6.09 11.10 6.39

EXAMPLE 33

N-[1-(1H-Benzimidazol-5-yl-methyl)-2-(4-methyl-piperidin-1-yl)-2-oxo-ethyl]-3'-amino-4-biphenylylsulphonamide Prepared from N-[1-((4-amino-3-nitro-phenyl)-methyl]-2-(4-methyl-piperidin-1-yl)-2-oxo-ethyl]-3'-nitro-4-biphenylyl-sulphonamide and reduction with catalytically actived hydrogen in the presence of palladium/charcoal in formic acid analogously to Example 1.

Yield: 6.3% of theory, Melting point: from 80° C. (decomp.) $C_{28}H_{31}N_5O_3S$ (517.66) Calculated: C 64.97 H 6.04 N 13.53 S 6.19 Found: 64.75 6.38 12.37 6.26

EXAMPLE 34

4-Cyclohexyl-N-[1-(1H-benzimidazol-5-yl-methyl)-2-(4-methyl-piperidin-1-yl)-2-oxo-ethyl]-benzenesulphonamide Prepared from 4-cyclohexyl-N-[1-((4-amino-3-nitrophenyl)-methyl)-2-(4-methyl-piperidin-1-yl)-2-oxoethyl]-benzenesulphonamide and cyclising with formic acid in the presence of palladium/charcoal analogously to Example 1.

Yield: 43% of theory, Melting point: 220°–225° C. $C_{28}H_{36}N_4O_3S$ (508.69) Calculated: C 66.12 H 7.13 N 11.01 S 6.30 Found: 66.06 7.07 11.01 6.12

EXAMPLE 35

N-[1-(1H-Benzimidazol-5-yl-methyl)-2-(4-methyl-piperidin-1-yl)-2-oxo-ethyl]-1,2,3,4-tetrahydroquinoline-8-sulphonamide Prepared from N-[1-(1H-benzimidazol-5-yl-methyl)-2-(4-methyl-piperidin-1-yl)-2-oxo-ethyl]-quinoline-8-sulphonamide by catalytic hydrogenation in the presence of palladium/charcoal in 50% acetic acid analogously to Example 1.

Yield: 67% of theory, Melting point: 126°–129° C. $C_{25}H_{31}N_5O_3S$ (481.62) Calculated: C 62.35 H 6.49 N 14.54 S 6.66 Found: 62.00 6.51 14.30 6.22

EXAMPLE 36

N-[1-(1H-Benzimidazol-5-yl-methyl)-2-(4-methyl-piperidin-1-yl)-2-oxo-ethyl]-quinoline-8-sulphonamide Prepared from 1-(1H-benzimidazol-5-yl-methyl)-2-(4-methyl-piperidin-1-yl)-2-oxo-ethylamine and quinoline-8-sulphonic acid chloride analogously to Example 2.

Yield: 27.0% of theory, Melting point: 123°–127° C. $C_{25}H_{27}N_5O_3S$ (477.59) Calculated: C 62.87 H 5.70 N 14.66 S 6.71 Found: 62.67 5.83 14.98 6.43

The following compound is obtained analogously:

N-[1-(1H-benzimidazol-5-yl-methyl)-2-(4-methyl-piperidin-1-yl)-2-oxo-ethyl]-3-methyl-quinoline-8-sulphonamide $C_{26}H_{29}N_5O_3S$ (491.62) Calculated: C 63.52 H 5.95 N 14.25 S 6.52 Found: 63.30 6.09 14.00 6.66

EXAMPLE 37

N-[1-(1H-Benzimidazol-5-yl-methyl)-2-(4-methyl-piperidin-1-yl)-2-oxo-ethyl]-naphthalene-1-sulphonamide Prepared from 1-(1H-benzimidazol-5-yl-ethyl)-2-(4-methyl-piperidin)-1-yl)-2-oxo-ethylamine and naphthalene-1-sulphonic acid chloride analogously to Example 2.

Yield: 38.0% of theory, Melting point: 80°–84° C. $C_{26}H_{28}N_4O_3S$ (476.60) Calculated: C 65.52 H 5.92 N 11.76 S 6.73 Found: 65.76 6.04 11.52 6.66

EXAMPLE 38

N-[1-(1H-Benzimidazol-5-yl-methyl)-2-(4-methyl-piperidin-1-yl)-2-oxo-ethyl]-2'-nitro-4-biphenylylsulphonamide Prepared from 1-(1H-benzimidazol-5-yl-methyl)-2-(4-methyl-piperidin-1-yl)-2-oxo-ethylamine and 2'-nitro-4-biphenylyl-sulphonic acid chloride analogously to Example 2.

Yield: 38.0% of theory, Melting point: from 215° C. $C_{28}H_{29}N_5O_5S$ (547.64) Calculated: C 61.41 H 5.34 N 12.79 Found: 61.37 5.38 12.82

EXAMPLE 39

4-Amino-N-[1-(1H-benzimidazol-5-yl-methyl)-2-(4-(N-acetyl-methylamino)-piperidin-1-yl)-2-oxo-ethyl]-3,5-dichloro-benzenesulphonamide Prepared from 4-amino-N-[1-(1H-benzimidazol-5-yl-methyl)-2-(4-methylamino-piperidin-1-yl)-2-oxo-ethyl]-3,5-dichloro-benzenesulphonamide and acetylchloride in dioxane and triethylamine analogously to Example 2.

Yield: 44.0% of theory, Melting point: from 150° C. (decomp.) $C_{24}H_{28}Cl_2N_6O_4S$ (567.50) Calc.: C 50.80 H 4.97 N 14.81 S 5.65 Cl 12.49 Found: 50.42 5.47 14.74 5.38 12.28

EXAMPLE 40

2-Carbethoxy-N-[1-(1H-benzimidazol-5-yl-methyl)-2-(4-methyl-piperidin-1-yl)-1,2,3,4-tetrahydro-isoquinoline-5-sulphonamide Prepared from N-[1-(1H-benzimidazol-5-yl-methyl)-2-(4-methyl-piperidin-1-yl)-1,2,3,4-tetrahydro-isoquinoline-5-sulphonamide and ethyl chloroformate in methylene chloride and triethylamine analogously to Example 2.

Yield: 16.4% of theory, Melting point: from 100° C. (decomp.) $C_{28}H_{35}N_5O_5S$ (553.69) Calculated: C 60.74 H 6.37 N 12.65 S 5.79 Found: 60.52 6.62 12.88 5.68

EXAMPLE 41

2-Acetyl-N-[1-(1H-benzimidazol-5-yl-methyl)-2-(4-methyl-piperidin-1-yl)-1,2,3,4-tetrahydro-isoquinoline-5-sulphonamide Prepared from N-[1-(1H-benzimidazol-5-yl-methyl)-2-(4-methyl-piperidin-1-yl)-1,2,3,4-tetrahydro-isoquinoline-5-sulphonamide and acetic anhydride analogously to Example 40.

Yield: 29.0% of theory, Melting point: from 145° C. (decomp.) $C_{27}H_{33}N_5O_4S$ (523.66) Calculated: C 61.93 H 6.35 N 13.37 S 6.12 Found: 61.80 6.60 13.50 6.01

EXAMPLE 42

4-Amino-N-[1-(1H-benzimidazol-5-yl-methyl)-2-(4-methyl-1,2,3,6-tetrahydro-pyridin-1-yl)-2-oxo-ethyl]-3,5-dichloro-benzenesulphonamide Prepared from 2-[N-(4-amino-3,5-dichloro-phenyl)-sulphamoyl]-3-(1H-benzimidazol-5-yl)-propionic acid and 4-methyl-1,2,3,6-tetrahydro-pyridine analogously to Example 15.

Yield: 33.0% of theory, Melting point: 117°–121° C. $C_{22}H_{23}Cl_2N_5O_3S$ (508.43) Calculated: C 51.97 H 4.56 N 13.77 Found: 52.19 4.71 13.41

EXAMPLE 43

4-Amino-N-[1-(1H-benzimidazol-5-yl-methyl)-2-(2-carbethoxy-4-methyl-piperidin-1-yl)-2-oxo-ethyl]-3,5-dichloro-benzenesulphonamide Prepared from 2-[N-(4-amino-3,5-dichloro-phenyl)-sulphamoyl]-3-(1H-benzimidazol-5-yl)-propionic acid and ethyl 4-methyl-piperidine-2-carboxylate analogously to Example 15.

Yield: 32.0% of theory, Melting point: from 110° C. (decomp.) $C_{25}H_{29}Cl_2N_5PO_5S$ (582.51) Calc.: C 51.55 H 5.02 N 12.02 S 5.50 Cl 12.17 Found: 51.84 5.16 11.87 5.76 12.23

EXAMPLE 44

4-Amino-N-[1-(1H-benzimidazol-5-yl-methyl)-2-(5,6,7,8-tetrahydro-thiazolo[4',5':5,4]thieno[3,2-c]pyridin-7-yl)-2-oxo-ethyl]-3,5-dichloro-benzenesulphonamide Prepared from 2-[N-(4-amino-3,5-dichloro-phenyl)-sulphamoyl]-3-(1H-benzimidazol-5-yl)-propionic acid and 5,6,7,8-tetrahydrothiazolo[4',5':5,4]thieno[3,2-c]-pyridine analogously to Example 15.

Yield: 49.0% of theory, Melting point: 160°–165° C. $C_{24}H_{20}Cl_2N_6O_3S_3$ (607.56) Calc.: C 47.45 H 3.32 N 13.83 S 15.83 Cl 11.67 Found: 47.31 3.66 13.64 14.13 11.45

EXAMPLE 45

4-Amino-N-[1-(1H-benzimidazol-5-yl-methyl)-2-(4,5,6,7-tetrahydro-thieno[3,2-c]pyridin-5-yl)-2-oxo-ethyl]-3,5-dichloro-benzenesulphonamide Prepared from 2-[N-(4-amino-3,5-dichloro-phenyl)-sulphamoyl]-3-(1H-benzimidazol-5-yl)-propionic acid and 4,5,6,7-tetrahydro-thieno[3,2-c]pyridine analogously to Example 15.

Yield: 22.0% of theory, Melting point: 236°–238° C. $C_{23}H_{21}Cl_2N_5O_3S_2$ (550.49) Calc.: C 50.18 H 3.85 N 12.72 S 11.65 Cl 12.88 Found: 49.99 3.87 12.56 11.38 12.77

EXAMPLE 46

4-Amino-N-[1-(1H-benzimidazol-5-yl-methyl)-2-(2,3,4,5,6,7-hexahydro-1H-azepin-1-yl)-2-oxo-ethyl]-3,5-dichloro-benzenesulphonamide Prepared from 2-[N-(4-amino-3,5-dichloro-phenyl)-sulphamoyl]-3-(1H-benzimidazol-5-yl)-propionic acid and hexahydro-azepine analogously to Example 15.

Yield: 18.6% of theory, Melting point: 261°–265° C. $C_{22}H_{25}Cl_2N_5O_3S$ (510.45) Calc.: C 51.77 H 4.94 N 13.72 S 6.28 Cl 13.89 Found: 51.77 5.06 13.85 6.16 13.70

EXAMPLE 47

4-Amino-N-[1-(1H-benzimidazol-5-yl-methyl)-2-(4-phenyl-1,2,3,6-tetrahydro-pyridin-1-yl)-2-oxo-ethyl]-3,5-dichloro-benzenesulphonamide Prepared from 2-[N-(4-amino-3,5-dichloro-phenyl)-sulphamoyl]-3-(1H-benzimidazol-5-yl)-Propionic acid and 4-phenyl-1,2,3,6-tetrahydro-pyridine analogously to Example 15.

Yield: 44.0% of theory, Melting point: from 175° C. (decomp.) $C_{27}H_{25}Cl_2N_5O_3S$ (570.50) Calc.: C 56.84 H 4.42 N 12.28 S 5.62 Cl 12.43 Found 56.90 4.50 12.30 5.81 12.36

EXAMPLE 48

4-Amino-N-[1-(1H-benzimidazol-5-yl-methyl)-2-(4,4-dimethyl-piperidin-1-yl)-2-oxo-ethyl]-3,5-dichloroben-zenesulphonamide Prepared from 2-[N-(4-amino-3,5-dichloro-phenyl)-sulphamoyl]-3-(1H-benzimidazol-5-yl)-propionic acid and 4,4-dimethyl-piperidine analogously to Example 15.

Yield: 53.0% of theory, Melting point: 247°–248° C. $C_{23}H_{27}Cl_2N_5O_3S$ (524.47) Calc.: C 52.67 H 5.19 N 13.35 S 6.11 Cl 13.52 Found: 52.51 5.26 13.56 6.30 13.78

EXAMPLE 49

4-Amino-N-[1-(1H-benzimidazol-5-yl-methyl)-2-(2-phenylmorpholin-4-yl)-2-oxo-ethyl]-3,5-dichloroben-zenesulphonamide Prepared from 2-[N-(4-amino-3,5-dichloro-phenyl)-sulphamoyl]-3-(1H-benzimidazol-5-yl)-propionic acid and 2-phenyl-morpholine analogously to Example 15.

Yield: 52.2% of theory, Melting point: from 230° C. $C_{26}H_{25}Cl_2N_5O_4S$ (574.49) Calc.: C 54.36 H 4.39 N 12.19 S 5.58 Cl 12.34 Found: 54.14 4.43 12.07 5.90 12.56

EXAMPLE 50

4-Amino-N-[1-(1H-benzimidazol-5-yl-methyl)-2-(2-amino-5,6,7,8-tetrahydro-thiazolo[4',5':5,4]thieno[3,2-c]-pyridin-7-yl)-2-oxo-ethyl]-3,5-dichlorobenzenesulphonamide Prepared from 2-[N-(4-amino-3,5-dichloro-phenyl)-sulphamoyl]-3-(1H-benzimidazol-5-yl)-propionic acid and 2-amino-5,6,7,8-tetrahydro-thiazolo[4',5':5,4]-thieno[3,2-c]pyridine analogously to Example 15.

Yield: 58% of theory, Melting point: 203°–207° C. $C_{24}H_{21}Cl_2N_7O_3S_3$ (622.58) Calc.: C 46.30 H 3.40 N 15.75 S 15.45 Cl 11.39 Found: 46.12 3.71 15.46 15.67 11.55

EXAMPLE 51

N-[1-(1H-Benzimidazol-5-yl-methyl)-2-(4-methyl-piperidin-1-yl)-2-oxo-ethyl]-2'-amino-4-biphenylylsulphonamide Prepared from N-[1-(1H-benzimidazol-5-yl-methyl)-2-(4-methyl-piperidin-1-yl)-2-oxo-ethyl]-2'-nitro-4-biphenylyl-sulphonamide in the presence of platinum/charcoal or Raney nickel and under a hydrogen pressure of 3 bar analogously to Example 22.

Yield: 28.0% of theory, Melting point: from 82° C. $C_{28}H_{31}N_5O_3S$ (517.66) Calc.: C 55.25 H 5.80 N 11.51 S 5.27 Cl 11.65 Found: 55.58 6.22 11.46 5.52 11.67

EXAMPLE 52

4-Amino-N-[1-(1H-benzimidazol-5-yl-methyl)-2-(2-carboxy-4-methyl-piperidin-1-yl)-2-oxo-ethyl]-3,5-dichlorobenzenesulphonamide Prepared by hydrolysis of 4-amino-N-[1-(1H-benzimidazol-5-yl-methyl)-2-(2-carbethoxy-4-methyl-piperidin-1-yl)-2-oxo-ethyl]-3,5-dichloro-benzenesulphonamide in the presence of 1N sodium hydroxide solution analogously to Example 24.

Yield: 61.0% of theory, Melting point: from 180° C. (decomp.) $C_{23}H_{25}Cl_2N_5O_5S$ (554.46) Calc.: C 49.82 H 4.54 N 12.63 S 5.78 Cl 12.79 Found: 49.65 4.56 12.53 5.41 13.00

EXAMPLE 53

N-[1-(1H-Benzimidazol-5-yl-methyl)-2-(4-methyl-piperidin-1-yl)-2-oxo-ethyl]-3-methyl-1,2,3,4-tetrahydro-quinoline-8-sulphonamide Prepared by catalytic hydrogenation of N-[1-(1H-benzimidazol-5-yl-methyl)-2-(4-methyl-piperidin-1-yl)-2-oxoethyl]-3-methyl-quinoline-8-sulphonamide in the presence of palladium/charcoal in 50% acetic acid and under a hydrogen pressure of 3 bar analogously to Example 35.

Yield: 68.0% of theory, Melting point: from 90° C. $C_{26}H_{33}N_5O_3S$ (495.65) Calculated: C 63.00 H 6.71 N 14.13 S 6.47 Found: 62.82 6.74 14.52 6.20

EXAMPLE 54

4-Amino-N-[1-(1H-benzimidazol-5-yl-methyl)-2-(4-carbethoxy-piperidin-1-yl)-2-oxo-ethyl]-3,5-dichlorobenzenesulphonamide Prepared from 2-[N-(4-amino-3,5-dichloro-phenyl)-sulphamoyl]-3-(1H-benzimidazol-5-yl)-propionic acid and ethyl piperidine-4-carboxylate analogously to Example 15.

Yield: 64% of theory, Melting point: 144°–148° C. $C_{24}H_{27}Cl_2N_5O_5S$ (568.48) Calc.: C 50.71 H 4.79 N 12.32 S 5.64 Cl 12.47 Found: 50.55 4.68 12.32 5.60 12.71

EXAMPLE 55

4-Amino-N-[1-(1H-benzimidazol-5-yl-methyl)-2-(4-carboxy-piperidin-1-yl)-2-oxo-ethyl]-3,5-dichlorobenzenesulphonamide Prepared from 4-amino-N-[1-(1H-benzimidazol-5-yl-methyl)-2-(4-carbethoxy-piperidin-1-yl)-2-oxo-ethyl]-3,5-dichloro-benzenesulphonamide and 1N sodium hydroxide solution analogously to Example 24.

Yield: 65% of theory, Melting point: 255°–256° C. (decomp.) $C_{22}H_{23}Cl_2N_5O_5S$ (540.43) Calc.: C48.90 H 4.29 N 12.96 S 5.93 Cl 13.12 Found: 48.73 4.17 12.85 5.63 13.02

EXAMPLE 56

4-Amino-N-[1-(1H-benzimidazol-5-yl-methyl)-2-(4-aminocarbonyl-piperidin-1-yl)-2-oxo-ethyl]-3,5-dichlorobenzenesulphonamide 540 mg (1 mMol) of 4-amino-N-[1-(1H-benzimidazol-5-yl-methyl)-2-(4-carboxy-piperidin-1-yl)-2-oxo-ethyl]-3,5-dichloro-benzenesulphonamide are dissolved in 10 ml of absolute dimethylformamide and combined, with stirring, with 180 mg (1.1 mMol) of carbonyl-diimidazole. After about one hour 2 ml of ethanolic ammonia solution are added dropwise and the mixture is stirred for a further 12 hours. It is then evaporated down, the residue is mixed with water and extracted twice with ethyl acetate. The organic phase is washed twice with aqueous saline solution, dried with sodium sulphate and evaporated down. The residue is purified over a silica gel column, the evaporated eluate is triturated with ether and suction filtered.

Yield: 170 mg (31.5% of theory), Melting point: from 210° C. (decomp.) Calc.: C 48.98 H 4.48 N 15.58 S 5.94 Cl 13.14 Found: 48.82 4.39 15.35 5.70 13.08

EXAMPLE 57

4-Amino-N-[1-(1H-benzimidazol-5-yl-methyl)-2-(4-cyano-piperidin-1-yl)-2-oxo-ethyl]-3,5-dichlorobenzenesulphonamide Prepared from 4-amino-N-[1-(1H-benzimidazol-5-ylmethyl)-2-(4-aminocarbonyl-piperidin-1-yl)-2-oxo-ethyl]-3,5-dichloro-benzenesulphonamide by reacting with phosphorusoxychloride at ambient temperature.

Yield: 70% of theory, Melting point: 231°–234° C. (decomp.) $C_{22}H_{22}Cl_2N_6O_3$ (521.43) Calc.: C 50.68 H 4.25 N 16.12 S 6.15 Cl 13.60 Found: 50.75 4.28 15.93 6.40 13.70

EXAMPLE 58

4-Amino-N-[1-(1H-benzimidazol-5-yl-methyl)-2-(4-hydroxy-piperidin-1-yl)-2-oxo-ethyl]-3,5-dichlorobenzenesulphonamide 410 mg (0.8 mMol) of 4-amino-N-[1-(1H-benzimidazol-5-yl-methyl)-2-(piperidin-4-on-1-yl)-2-oxo-ethyl]-3,5-dichloro-benzenesulphonamide are dissolved in 8 ml of absolute dimethylformamide, mixed with 100 mg (2.6 mMol) of sodium borohydride and left to stand for 12 hours at ambient temperature. Then the reaction mixture is poured into water and extracted 3 times with ethyl acetate. The organic phase is washed twice with water, dried with sodium sulphate and evaporated down. The residue is purified over a silica gel column, the evaporated eluate is triturated with ether and suction filtered.

Yield: 230 mg (56% of theory), Melting point: 241°–243° C. (decomp.) $C_{21}H_{23}Cl_2N_5O_4S$ (512.42) Calc.: C 49.22 H 4.52 N 13.66 S 6.26 Cl 13.84 Found: 48.92 4.70 13.44 6.37 14.09

EXAMPLE 59

4-Amino-N-[1-(1H-benzimidazol-5-yl-methyl)-2-(4-methyl-piperazin-1-yl)-2-oxo-ethyl]-3,5-dichlorobenzenesulphonamide Prepared from 2-(4-amino-3,5-dichlorobenzenesulphamoyl)-2-(1H-benzimidazol-5-yl)-propionic acid and N-methylpiperazine analogously to Example 15.

Yield: 69% of theory, Melting point: 237°–240° C. (decomp.) Calc.: C 49.32 H 5.73 N 16.43 S 6.27 Cl 13.86 Found: 49.31 5.71 15.37 6.30 13.55

EXAMPLE 60

4-Amino-N-[1-(1H-benzimidazol-5-yl-methyl)-2-(4-methylamino-piperidin-1-yl)-2-oxo-ethyl]-3,5-dichlorobenzenesulphonamide 2.05 g of 4-amino-N-[1-(1H-benzimidazol-5-yl-methyl)-2-(piperidin-4-on-1-yl)-2-oxo-ethyl]-3,5-dichlorobenzenesulphonamide are dissolved in 20 ml of ethanol and combined with 30 ml of ethanolic methylamine solution. Then 310 mg of sodium cyanoborohydride and 240 mg of glacial acetic acid are added and the mixture is stirred at ambient temperature for 4 hours. Then half the amount of reducing agent is added and the mixture is stirred overnight. The precipitate formed is chromatographed over a silica gel column (eluant: methylene chloride/methanol/ammonia=8:2:0.2). 1.2 g of product are obtained which are recrystallised from a little ethanol.

Yield: 1.05 g (46% of theory), $C_{22}H_{26}N_6Cl_2O_3S$ (525.46) Calculated: C 50.44 H 5.64 N 14.70 Found: 49.54 5.68 14.62

We claim:

1. A benzimidazolyl derivative of the formula I

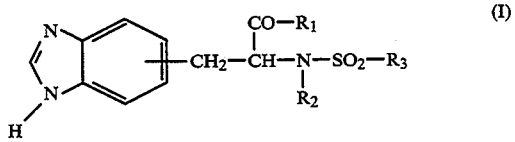

wherein:

R₁ denotes a piperidino group optionally substituted by a phenyl, hydroxy, carboxy, alkylcarbonyl, aminocarbonyl, cyano or N-alkanoyl-alkylamino group, wherein the hydroxy group may not be in the α-position to the ring nitrogen atom, wherein said piperidino group may additionally be substituted by an alkyl group and, in addition, the methylene group in the 4-position of the piperidino group may be replaced by a carbonyl group, or an ethylene group in the 3,4-position of the piperidino group may be replaced by an ethenylene group;

a piperidino group substituted by three alkyl groups wherein the alkyl substituents may be identical or different;

$R_2$ denotes a hydrogen atom or an alkyl group; and, $R_3$ denotes a phenyl group optionally substituted by a fluorine, chlorine or bromine atom or by an alkyl, nitro, amino, alkylamino, dialkylamino, phenyl or cyclohexyl group, whilst the phenyl substituent may also be substituted by a fluorine, chlorine or bromine atom or by a nitro or amino group;

a phenyl group disubstituted by fluorine, chlorine or bromine atoms or by alkyl or alkoxy groups, whilst one of the substituents may also denote a nitro or amino group;

a phenyl group substituted by a hydroxy, amino, alkylamino, dialkylamino or pyrrolyl group, whilst at the same time the phenyl group is substituted by two chlorine or bromine atoms or by two $C_{1-4}$-alkyl groups and the pyrrolyl group may be substituted by one or two alkyl groups;

a naphthyl group optionally mono- or disubstituted by hydroxy, alkoxy or dialkylamino groups;

an optionally alkyl-substituted indanyl group;

whilst, unless otherwise specified, the alkyl, alkanoyl and alkoxy moieties mentioned in the definition of groups $R_1$ to $R_3$ may each contain 1 to 3 carbon atoms;

or a pharmaceutically acceptable salt thereof.

2. A benzimidazolyl derivative of the formula I according to claim 1, wherein:

$R_1$ denotes a piperidino group optionally substituted in the 4-position by a $C_{1-3}$-alkyl group or by a hydroxy, cyano, aminocarbonyl, methylamino or N-acetyl-methylamino group, a piperidino group substituted by two or three methyl groups, a 4-methyl-piperidino group substituted by a carboxy, methoxycarbonyl or ethoxycarbonyl group;

or a 4-methyl-1,2,3,6-tetrahydro-pyridino group, $R_2$ denotes a hydrogen atom or a methyl group; and, $R_3$ denotes a phenyl group optionally substituted by a chlorine atom or by a methyl, nitro, amino, phenyl or cyclohexyl group, whilst the phenyl substituent may also be substituted by a fluorine atom or by a nitro or amino group;

a phenyl group disubstituted by chlorine atoms or by methyl groups, wherein the substituents may be identical or different and additionally one of the substituents may denote a nitro or amino group;

a phenyl group substituted by a hydroxy, amino, methylamino, ethylamino, dimethylamino or pyrrolyl group, whilst at the same time the phenyl group is substituted by two chlorine atoms or by two $C_{1-4}$-alkyl groups;

a naphthyl group optionally mono- or disubstituted by hydroxy, methoxy or dimethylamino groups;

an optionally methyl-substituted indanyl group;

or a pharmaceutically acceptable salt thereof.

3. A benzimidazolyl derivative of the formula I according to claim 1, wherein:

the benzimidazolyl group is substituted in the 5-position;

$R_1$ denotes a piperidino group optionally substituted in the 4-position by a $C_{1-3}$-alkyl group, a 4-methyl-piperidino group substituted in the 2-position by a carboxy, methoxycarbonyl or ethoxycarbonyl group;

or a 4-methyl-1,2,3,6-tetrahydro-pyridino group, $R_2$ denotes a hydrogen atom; and, $R_3$ denotes a phenyl group substituted by a hydroxy, amino, methylamino, ethylamino, dimethylamino or pyrrolyl group, whilst at the same time the phenyl group is substituted by two chlorine atoms or by two tert.butyl groups;

a 4-biphenylyl group;

a naphthyl group substituted by a dimethylamino group;

or a pharmaceutically acceptable salt thereof.

4. A compound selected from the group consisting of:
(a) 4-amino-N-[1-(1H-benzimidazol-5-yl-methyl)-2-(4-ethyl-piperidin-1-yl)-2-oxo-ethyl]-3,5-dichloro-benzenesulphonamide,
(b) N-[1-(1H-benzimidazol-5-yl-methyl)-2-(4-ethyl-piperidin-1-yl)-2-oxo-ethyl]-3,5-dichloro-4-ethylamino-benzenesulphonamide,
(c) 4-amino-N-[1-(1H-benzimidazol-5-yl-methyl)-2-(piperidin-4-on-1-yl)-2-oxo-ethyl]-3,5-dichloro-benzenesulphonamide,
(d) 4-amino-N-[1-(1H-benzimidazol-5-yl-methyl)-2-(4-methyl-piperidin-1-yl)-2-oxo-ethyl]-3,5-dichloro-benzenesulphonamide, and the pharmaceutically acceptable salts thereof.

5. 4-Amino-N-[1-(1H-benzimidazol-5-yl-methyl)-2-(4-methyl-piperidin-1-yl)-2-oxo-ethyl]-3,5-dichloro-benzenesulphonamide, or a pharmaceutically acceptable salt thereof.

6. A pharmaceutical composition comprising a thrombin inhibiting effective amount of a compound according to claims 1, 2, 3, 4, or 5 in admixture with one or more inert carriers and/or diluents.

7. A method for treating deep leg thrombosis, reocclusions after bypass operations or percutaneous transluminal coronary angioplasty, pulmonary embolism, or disseminated intravascular coagulation, which method comprises administering to a mammal having such condition or which is susceptible thereto an anti-thrombotic amount of a compound according to claims 1, 2, 3, 4, or 5.

* * * * *